United States Patent [19]
Anderson et al.

[11] Patent Number: 6,065,472
[45] Date of Patent: May 23, 2000

[54] MULTIDOSE POWDER INHALATION DEVICE

[75] Inventors: Gregor John McLennan Anderson; Richard Ian Walker, both of Hertford; Michael Birsha Davies, Ware; Philip William Farr, Hertford, all of United Kingdom

[73] Assignee: Glaxo Wellcome Inc., Research Triangle Park, N.C.

[21] Appl. No.: 09/101,102

[22] PCT Filed: Dec. 19, 1996

[86] PCT No.: PCT/GB96/03141

§ 371 Date: Jul. 16, 1998

§ 102(e) Date: Jul. 16, 1998

[87] PCT Pub. No.: WO97/25086

PCT Pub. Date: Jul. 17, 1997

[30] Foreign Application Priority Data

Jan. 3, 1996 [GB] United Kingdom .................... 9600044
Dec. 3, 1996 [GB] United Kingdom .................... 9625134

[51] Int. Cl.[7] .......................... A51M 15/00; A51M 11/00
[52] U.S. Cl. ................................ 128/203.21; 128/203.12; 128/203.15; 128/200.18
[58] Field of Search ........................ 128/203.21, 203.12, 128/203.15, 200.23, 200.14, 200.24, 204.25, 200.18

[56] References Cited

U.S. PATENT DOCUMENTS 3,288,277  11/1966  Hallerbach .
3,437,236   4/1969  Huck .
4,907,583   3/1990  Wetterlin et al. .
5,035,237   7/1991  Newell et al. ....................... 128/203.15
5,388,572   2/1995  Mulhauser et al. ................. 128/203.15
5,492,112   2/1996  Mecikalski et al. ................ 128/203.21
5,622,166   4/1997  Eisele et al. ........................ 128/203.21
5,676,130  10/1997  Gupte et al. ........................ 128/203.15
5,724,959   3/1998  McAughey et al. ................ 128/203.15
5,896,855   4/1999  Hobbs et al. ....................... 128/203.21

FOREIGN PATENT DOCUMENTS 0 558 879   9/1993   European Pat. Off. .
42 08 880   9/1993   Germany .
2 264 237   8/1993   United Kingdom .

Primary Examiner—John G. Weiss
Assistant Examiner—Todd M. Martin
Attorney, Agent, or Firm—James P. Riek; Sian C Hockley

[57] ABSTRACT

A powder inhalation device comprising a housing containing a pharmacologically active compound, a conduit (8) with an outlet extending into the housing through which a user can inhale to create an airflow through the conduit, a dosing unit (6,7) for delivering a dose of the compound to the conduit and baffles (9) arranged within the said conduit to aid disintegration of powder agglomerates entrained in said airflow. The baffles (9) comprise a plurality of staggered plates extending into the conduit from opposite sides of the conduit at an angle of less than 90° to the sides of the conduit and are inclined towards the outlet to create a plurality of constrictions within the conduit and a plurality of changes in the direction of the said airflow through the conduit.

28 Claims, 6 Drawing Sheets

MULTIDOSE POWDER INHALATION DEVICE

FIELD OF THE INVENTION

This invention relates to an inhalation device by means of which metered doses of medicament in the form of a powder can be dispensed to a user.

BACKGROUND OF THE INVENTION

Inhalation devices are known to be used for local administration of drugs to the respiratory tract and lungs of patients. One such device for use with blister packs in which the medicament is held in powder form in the blisters thereof is known as the DISKHALER inhalation device and is described in UK Patent No. 2178965. In use, a fresh blister is indexed to bring it into registration with a use station and then punctured with a puncturing member in two distinct actions to enable the medicament to be inhaled therefrom.

Another inhalation device described in UK Patent No. 2242134 is for use with peelable medicament packs defining containers for holding the medicament and includes a means for peeling the medicament pack apart to open each container in turn as they are brought into registration with a use station. This device is somewhat complex and contains many components.

Medicament for administration by inhalation should be of a controlled particle size in order to achieve maximum penetration in to the lungs, preferably in the range of 1 to 10 micrometers in diameter and more preferably 1 to 5 micrometers. Unfortunately, powders in this particle size range, hereinafter referred to as fine powders, for example micronised powders, usually have very poor flow characteristics due to the cohesive forces between the individual particles which make them readily agglomerate together to form bridges which are not readily broken apart to become free flowing. These characteristics create handling and metering difficulties which adversely affect the accurate dispensing of doses of the powder. However, co-pending PCT Patent Application No. EP96.03274 (filed in the United States as U.S. patent application Ser. No. 09/000093 on Feb. 2, 1998) describes how, by careful sizing of fine agglomerated powder, it is possible to make use of the cohesive forces between the particles to create agglomerates of powder which are free flowing. These agglomerates of powder can be easily handled and may be used to conveniently fill devices.

However, for efficient delivery to the lungs, the powder agglomerates must be broken down before they leave such a device, back into a controlled size.

It has been found that it is possible to break up powder agglomerates in the airflow as a user inhales by incorporating a series of baffles in the mouthpiece of a powder inhalation device. EP 0 237 507 describes baffles which comprise helical channel portions which give the airflow a rotating, helical pattern of motion.

However, one disadvantage associated with the baffles described in EP 0 237 507 in that the baffles comprise a number of components rendering the device manufacturing process relatively complicated and expensive.

GB 2191718 relates to aerosol devices for dispensing nicotine. The nicotine dispensing device has an impaction means designed to separate the spray allowing the smaller particles and vapour phase to flow around the baffle while the larger particles are removed.

PCT/EP93/00582 also describes a device comprising baffles which are acting as separators, but if the aerosol contains larger particles in the form of relatively loose agglomerates, these agglomerates are reduced in size if their velocity of impact against the baffles is sufficiently high.

One disadvantage of the two sets of baffles described in GB 2191718 and PCT/EP93/00582 is the high deposition of powder which can occur due to the baffles extending from the walls of the device at 90° to the direction of airflow. This may result in deposition of the larger agglomerates of powder occurring, which agglomerates could become loose in subsequent inhalations and result in variations in dosage.

It is an object of the invention to provide a device of the type just described which is simple for a user to operate and which is not unduly complex in its assembly. It is a further object to provide a device which may be filled with powder agglomerates but will deliver powder in a form suitable for administration by inhalation.

SUMMARY OF THE INVENTION

According to the present invention there is provided an inhalation device comprising a housing, an outlet through which a user can inhale, a medicament holder defining at least one pocket for containing a single dose of medicament in the form of a powder, a closure member having at least one closure pad resiliently urged into contact with the medicament holder to close the said at least one pocket, means for moving the pocket into registration with the outlet and means for lifting the closure pad away from the medicament holder to open the pocket when the pocket is brought into registration with the outlet.

Such a device is simple to operate requiring only one distinct action to enable the medicament to be inhaled therefrom. The device may also comprise relatively few components.

According to the invention there is also provided a powder inhalation device comprising a housing containing a pharmacologically active compound or medicament, a conduit with an outlet extending into the housing through which a user can inhale to create an airflow through the conduit, a dosing unit for delivering a dose of the compound to the conduit and baffles arranged within the said conduit to aid disintegration of powder agglomerates entrained in said airflow, characterised in that the baffles comprise a plurality of staggered plates extending into the conduit from opposite sides of the conduit at an angle of less than 90° to the sides of the conduit and are inclined towards the outlet to create a plurality of constrictions within the conduit and a plurality of changes in the direction of the said airflow through the conduit.

By use of this arrangement it is possible to provide baffles which are simple to manufacture and provide low deposition of powder, and yet which give good results in breaking agglomerates down into discrete constituent particles to create a powder of respirable size.

Preferably the device contains at least 2 plates and more preferably 4 plates.

Preferably the said plates are inclined at an angle less than 70° to the longitudinal axis of the conduit in the direction of airflow and more preferably the said plates are inclined at an angle in the range of 15° to 50°.

Suitably the penultimate baffle is shaped so that at some point along the plate it divides into at least 2 faces, the first face of which continues to extend into the conduit and a second face of which extends towards the outlet substantially parallel to the longitudinal axis of the conduit. This enables the airflow to exit parallel to the said axis delivering the powder directly to the user's respiratory tract and not into the cheek cavity of the user.

DESCRIPTION OF THE DRAWINGS

An embodiment of the invention is further described below with reference to the accompanying drawings in which.

DETAILED DESCRIPTION

Figure 1:
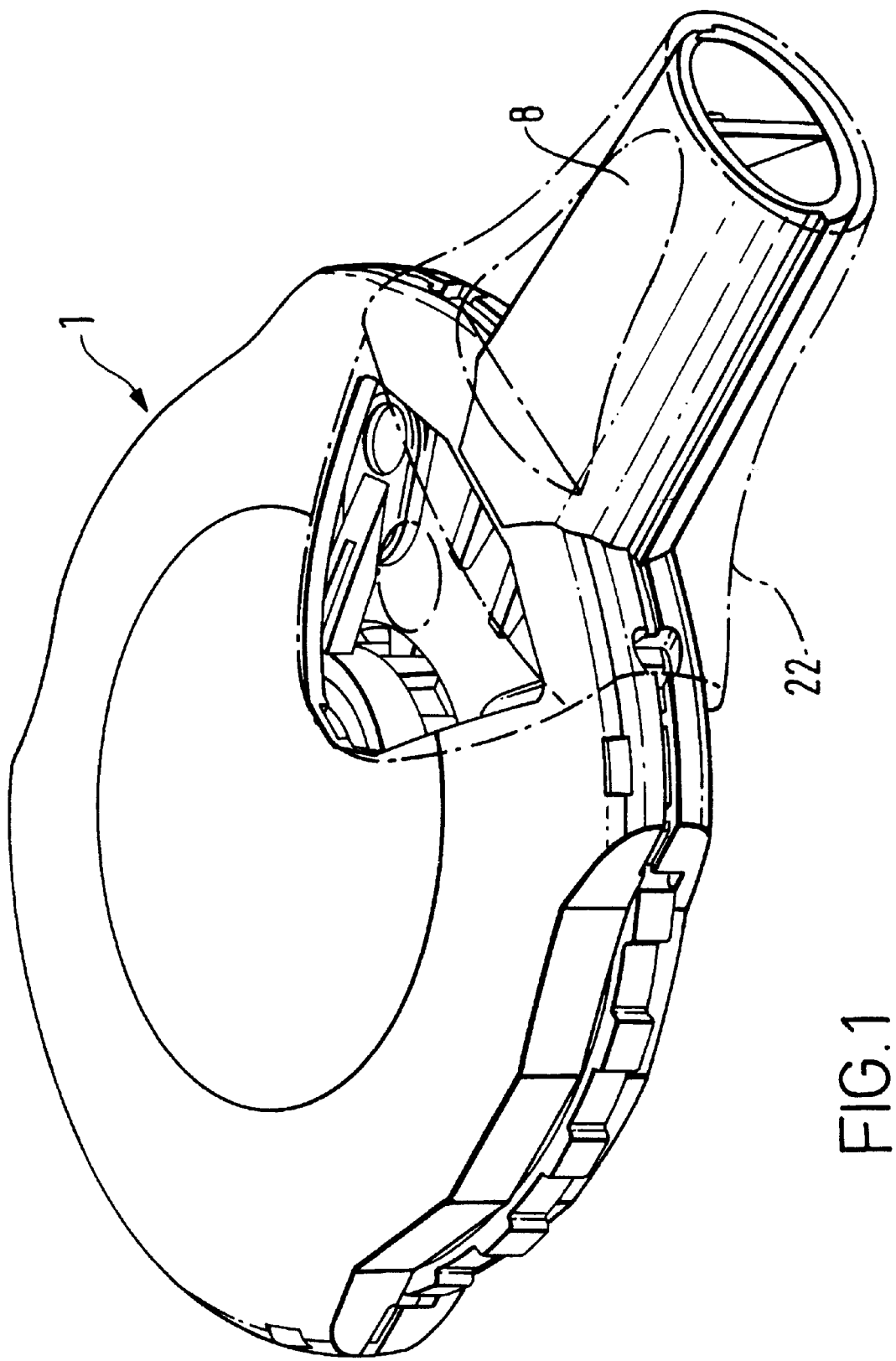
FIG. 1 is a perspective view of an assembled device according to the invention.
Figure 2:
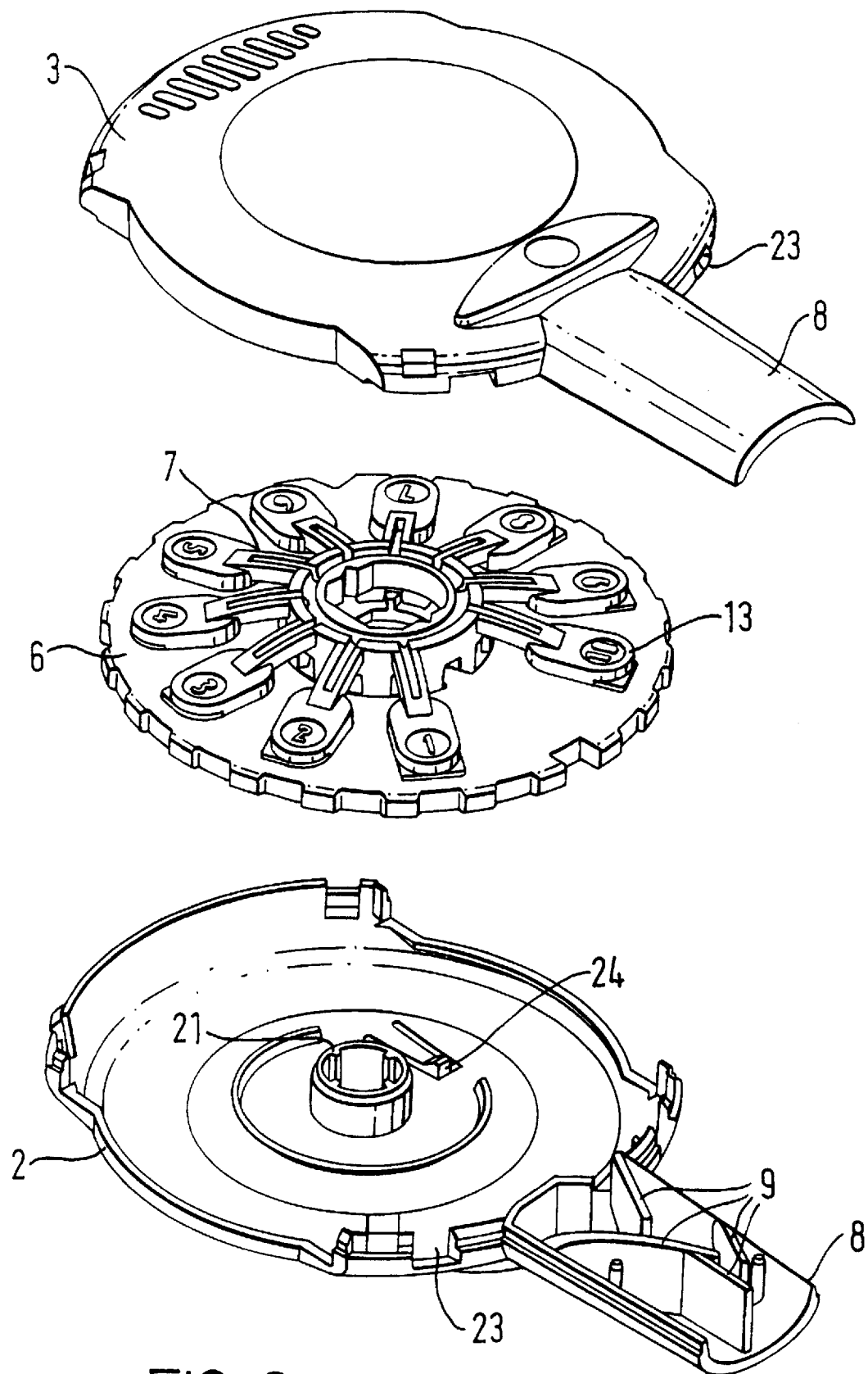
FIG. 2 is an exploded perspective view of the device of FIG. 1 showing the main body components and primary pack.
Figure 3:
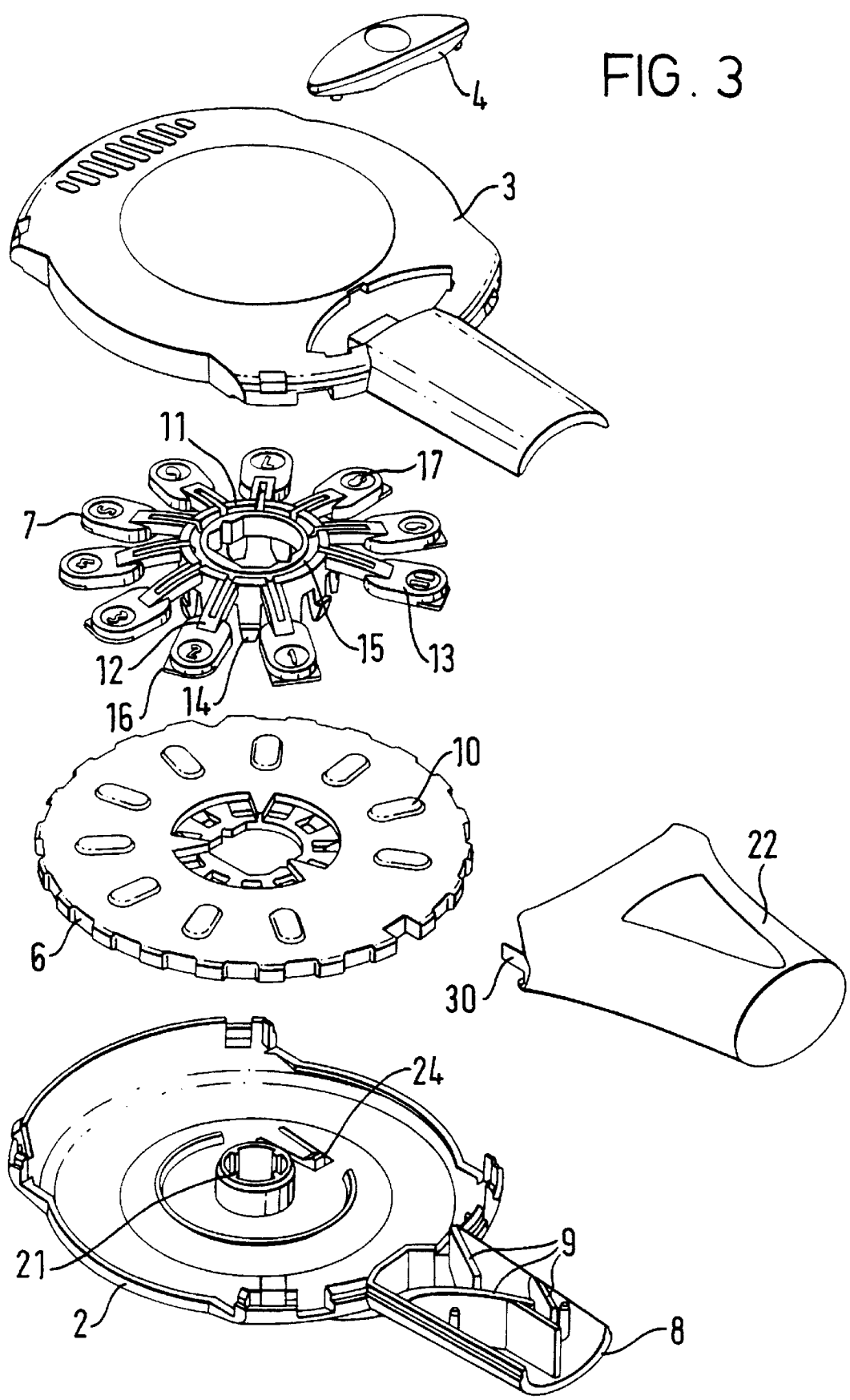
FIG. 3 is an exploded perspective view of the device showing each component in disassembled form.

The device shown in FIGS. 1 to 3 comprises a body 1 formed of a body base 2 and a body top 3, both of which may be moulded from a plastics material such as acryl-butyl styrene (ABS). Body top 3 is formed with window 4 the purpose of which is described below. The body 1 defines a main housing section adapted to contain a primary pack comprising a dose ring 6 and closure means in the form of a spider 7, and a mouthpiece section 8 forming an outlet through which a user can inhale extending radially from the main housing section. As seen in FIG. 2, the mouthpiece section 8 of body base 2 is formed with a plurality of baffles 9 which are explained below.

A medicament holder in the form of a disk or dose ring 6 comprises an upper surface formed with a plurality of cavities or pockets 10 for containing inhalable powdered medicament to be dispensed from the device. Each pocket 10 is surrounded by a raised lip (not shown). The dose ring shown is provided with ten pockets 10 which might be suitable for containing ten days' supply of medicament or sufficient medicament for a single course of treatment. It will be understood that the dose ring might have more or fewer pockets depending on the medicament to be contained. Suitable powdered medicaments are, for example, for the treatment of asthma, and include salbutamol, beclomethasone, salmeterol, fluticasone, formoterol, terbutaline, budesonide and flunisolide, and physiologically acceptable salts, solvates and esters or any combination thereof. Preferred medicaments are salbutamol, salbutamol sulphate, salmeterol, salmeterol xinafoate, fluticasone propionate, beclomethasone dipropionate or solvates thereof and terbutaline sulphate. Other suitable powdered medicaments include antiviral medicaments, for example zanamivir (4-guanidino-Neu-5-Ac-2-en). It will be appreciated by those skilled in the art that the powder medicament, may, if desired, be a combination of two or more active ingredients. A dose may be constituted from the contents of one or more cavities and the size of each cavity will depend on the dose to be delivered. It is to be understood that the medicament powder may consist purely of one or more active ingredients, or there may additionally be a carrier, for example lactose powder.

The dose ring 6 may be adapted for filling with agglomerated powder in accordance with the method and apparatus described in co-pending PCT Patent Application No. EP96.03274 (filed in the United States as U.S. patent application Ser. No. 09/000093 on Feb. 2, 1998).

The dose ring 6 has a stepped peripheral edge the purpose of which is explained below, and a splined hole in the center for engagement with the spider 7. The dose ring may also be moulded from a plastics material such as ABS.

The spider 7 comprises a central ring shaped section 11 from which extend a plurality of resilient radial arms 12, the number of which corresponds to the number of pockets 10 in the dose ring 6. Each radial arm 12 terminates in a pocket closure pad 13. A plurality of short resilient hooked tabs 14 extend axially from the central ring shaped section 11 and are adapted to form a snag fit with the dose ring 6 by engaging with the splined hole in the center of the dose ring 6. The spider 7 may be moulded from a plastics material such as polycarbonate or any other engineering plastics which has the required resiliency characteristics. When the spider 7 is assembled to the dose ring 6 to form the dosing unit or primary pack, the hooked tabs 14 tightly engage the splined hole in the dose ring 6 and each pocket closure pad 13 is resiliently urged into contact with a respective raised lip on the upper surface of the dose ring 6 by means of the resilient radial arms 12 in such a position as to cover and seal a respective pocket 10 to prevent loss of medicament from and ingression of moisture into the pocket. The pocket closure pads may be moulded with a smooth flat contact face which seals directly on the upper surface of the dose ring 6 or raised lip 28 (FIG. 6), or alternatively may be provided with a soft sealing material such as a thermoplastic elastomer, eg SANTOPRENE (Bayer), formed on the contact face to improve the sealing characteristics. To manufacture the spider 7 with a different sealing material on the pocket closure pad the spider may be moulded with a channel 15 formed in the upper face of the central ring shaped section 11 and in each radial arm 12, and a small hole (not shown) leading from the end of the channel 15 in each arm 12 through to the underside of the pocket closure pads 13. The sealing material in a molten state may then be made to flow round channel 15 and through the holes to the underside of each of the pocket closure pads 13 to form an integral cushion seal on each pad upon cooling.

The upper faces of the pocket closure pads 13 may have a number 17 or other indicating means moulded or printed thereon to give an indication as to how many doses of medicament remain in the device as is explained further below.

An edge of each pocket closure pad 13 is formed with a tab 16 adapted for engagement with a ramp 20 (FIGS. 4 and 5) integrally formed with body top 3 to effect opening of the pocket as explained below.

The primary pack fits into the main housing section of the body 1 as shown in FIGS. 2 and 3 such that axle 21 of body base 2 is located within the hole in the primary pack and the stepped peripheral edge of the dose ring protrudes through two cut away sections on opposite sides of the main housing section. Pawl 24 on body base 2 engages with teeth (not shown) on the underside of dose ring 6 to create a ratchet mechanism which only allows movement of the dose ring in one direction.

Pockets 10 may be filled with agglomerated powder as described in PCT patent application no. PCT EP96.03274. When so filled, for inhalation therapy it is essential that the largest possible quantity of primary particles inhaled is in the respirable range, that is smaller than 5 microns. In order to aid break-up of any powder agglomerates entrained in the air flow a series of baffles 9 are located in the mouthpiece section 8. As will be explained later, the position of the baffles are important. The baffles can be formed in a single moulding with the body, so affording consistent, controlled and repeatable tolerance. It will be understood that the number and exact dimensions of baffles present will depend on the powder being used and the strength of the forces holding the agglomerates together. For example, it has been found that four baffles achieved the required break up of powder agglomerates of zanamivir. It would be entirely straight forward for a skilled person to experiment with the baffle dimensions to obtain desired flow resistance for a particular powder.

Figure 4:
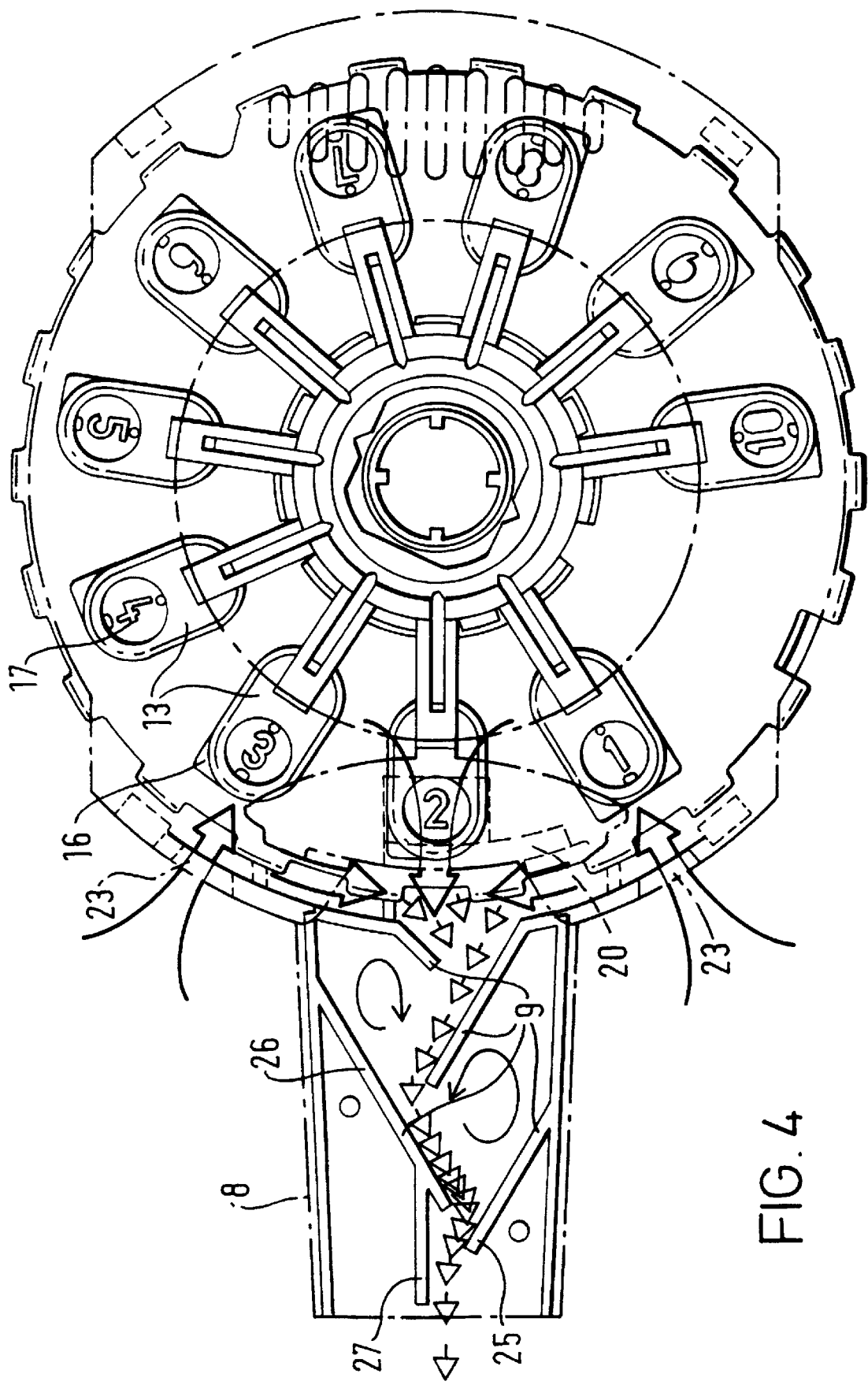
FIG. 4 is a plan view partly in section showing air flow through a preferred embodiment of the invention.
Figure 5:
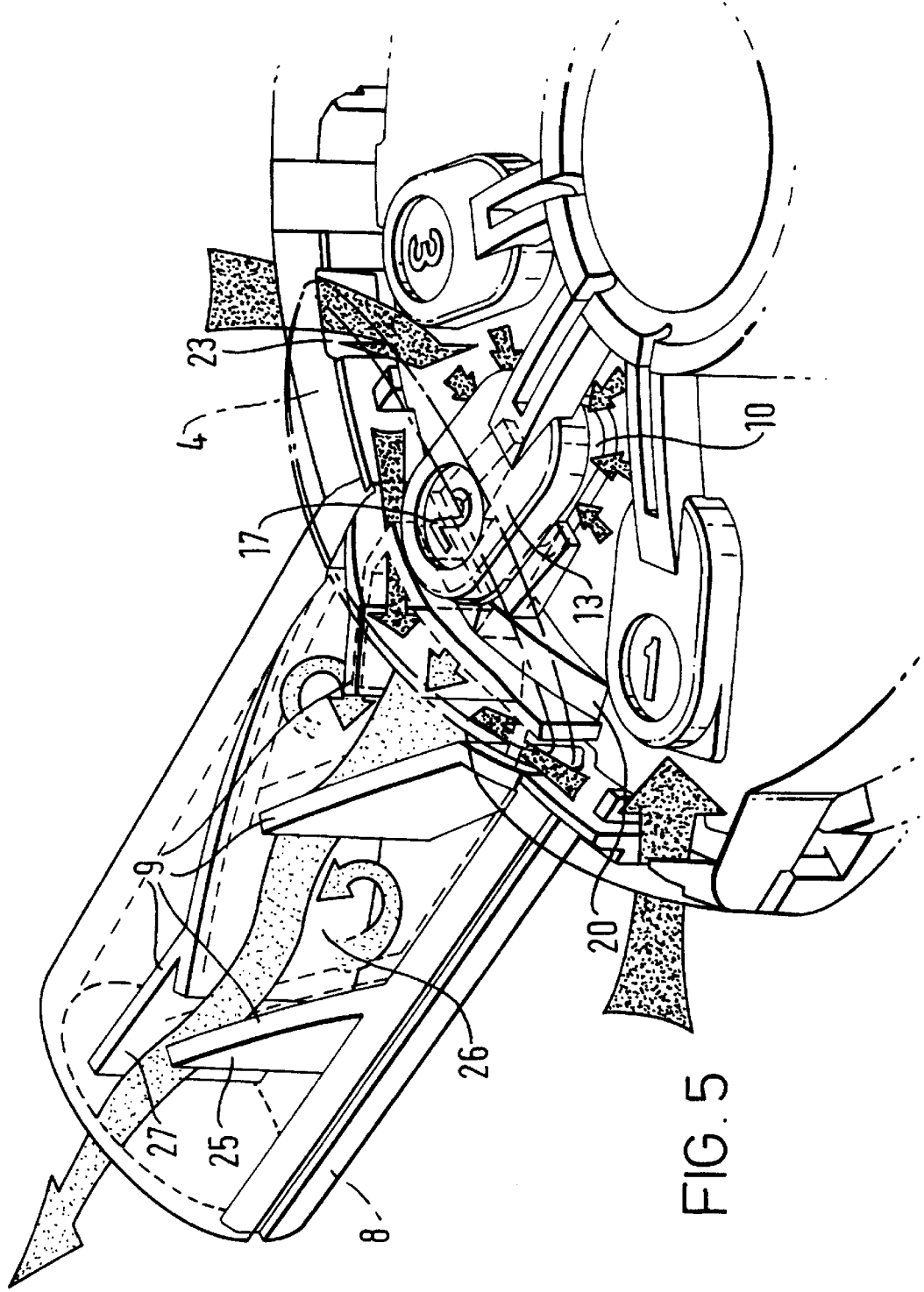
FIG. 5 is a perspective view showing airflow through the device shown in FIG. 4.

FIGS. 4 and 5 show a preferred arrangement of baffles 9 comprising of a plurality of staggered flat plates which extend into the conduit at angles of 30° to the longitudinal axis of the conduit from opposite sides of the housing. Most of the baffles extend beyond the longitudinal axis of the conduit with the final baffle 25 in the direction of airflow stopping short of the axis. The penultimate baffle 26 in the direction of the airflow has an extended flat face 27 running parallel to the longitudinal axis of the conduit and extending towards the outlet. This enables the airflow to exit parallel to the said axis delivering the powder directly to the user's respiratory tract and not into the cheek cavity of the user.

A mouthpiece cover 22 is adapted to fit over the mouthpiece section 8 when the device is not in use to prevent contamination of the mouthpiece by dust. The mouthpiece cover has two pins 30 adapted to pass through two slots 23 into the main housing section of body 1 either side of the mouthpiece section 8 to engage the stepped peripheral edge of the dose ring and so lock the primary pack to prevent accidental movement thereof when the device is not in use. To operate the device the user first removes mouthpiece cover 22 thereby unlocking the primary pack. The user then indexes a pocket to bring it into registration with the mouthpiece by holding the stepped peripheral edge of the dose ring where it protrudes through the cut away sections of the main housing section and rotating the dose ring 6 relative to the body 1. The ratchet mechanism described above allows rotation of the primary pack in one direction only. As the primary pack rotates, tab 16 of the next pocket closure pad 13 engages ramp 20 and pocket closure pad 13 is lifted away from the upper surface of the dose ring 6 as the tab rides over the ramp. As the pocket comes into registration with the mouthpiece, the raised lip 28 (FIG. 6) surrounding the pocket 10 engages with the sides of the exit channel 29 creating an increased resistance to motion of the dose ring, so giving a clear indication to the user that the dose ring is in position ready for delivery of medicament.

Figure 6:
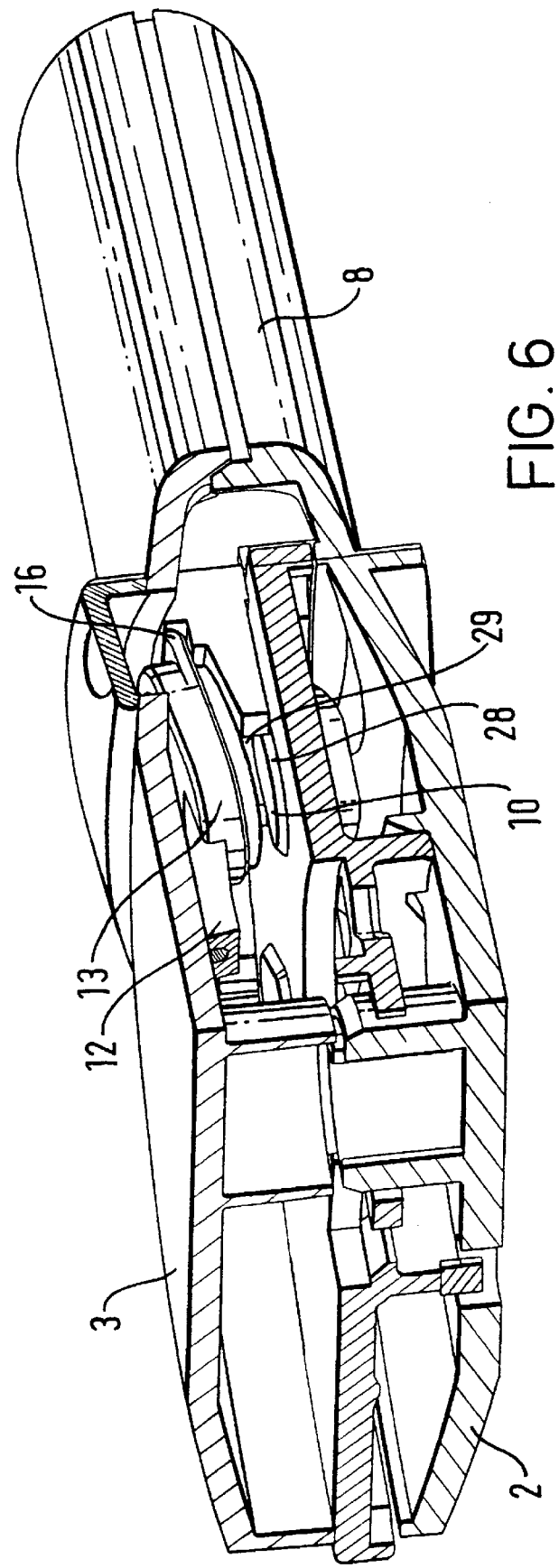
FIG. 6 is a cut away view showing the pocket closure pad held in the raised position

As the raised lip 28 surrounding the pocket 10 engages with the exit channel 29 the pocket closure pad 13 is in a raised position clear of the upper surface of the dose ring 6 as shown in FIG. 6. In this position, pocket closure pad 13 is situated directly beneath window 4 in body top 3 such that the number 17 or other dose indicating means moulded or printed on the upper face of the pocket closure pad 13 is clearly visible through window 4. This allows the user to see how many doses remain in the device.

The dose of medicament contained in pocket 10 is now ready for delivery. The user inhales through mouthpiece 8. Air is drawn into the device via slots 23 and directed over the open pocket 10 as seen in FIGS. 4 and 5. As the air flows over pocket 10, medicament powder in the pocket is entrained in the turbulent air flow, drawn through the mouthpiece section 8 and inhaled by the user.

As seen in FIG. 5, baffles 9 are arranged to disrupt the smooth flow of air through the mouthpiece to create additional turbulence, cause the air flow to change direction several times to cause any agglomerates of powder to collide with the baffles, walls and other agglomerates, and constrict the air flow to increase the flow velocity. The air circulation produces eddy currents in the back waters of the baffles creating further collisions to aid in the break up of the powder agglomerates. This is shown by the arrows representing air flow in FIG. 5. All of these effects promote the disintegration of powder agglomerates entrained in the air flow to render the powder in a form suitable for inhalation therapy. The extended flat face 27 running parallel to the longitudinal axis of the conduit attached to the penultimate baffle in the direction of airflow enables the airflow to exit parallel to the said axis delivering the powder directly to the user's respiratory tract and not into the cheek cavity of the user.

After inhalation the user replaces mouthpiece cover 22 to protect and lock the device until the next dose is required to be delivered.

It will be understood that the present disclosure is for the purpose of illustration only and the invention extends to modifications, variations and improvements thereto.

What is claimed is:

1. An inhalation device comprising a housing, an outlet through which a user can inhale, a medicament holder defining a pocket for containing a single dose of medicament in the form of a powder, a closure member having a closure pad resiliently urged into contact with the medicament holder to close said pocket, the closure pad and holder acting to contain the medicament, means for moving the pocket into registration with the outlet and means for lifting the closure pad away from the medicament holder to open the pocket when the pocket is brought into registration with the outlet, wherein the rotation of the medicament holder causes the closure pad to be lifted away from the medicament holder.

2. A device as claimed in claim 1, wherein said medicament holder comprises a disk which is rotatably mounted in the device with the said pocket arranged on one face of the said disk.

3. A device as claimed in claims 1, wherein said closure pad is resiliently urged into contact with the medicament holder by a respective resilient arm.

4. A device as claimed in claim 3 comprising a plurality of closure pads, wherein the closure member comprises a plurality of resilient arms connected together in the form of a spider.

5. A device as claimed in claim 4, wherein said spider is made from polycarbonate.

6. A device as claimed in claim 1, wherein said closure pad comprises a thermoplastic elastomer.

7. A device as claimed in claim 2, wherein said disk possesses an outer edge extending radially from an axis of rotation of said disk, and said edge externally protrudes from the body of the device to provide a means for moving the pocket into registration with the outlet.

8. A device as claimed in claim 7, wherein said disk is provided with grips at its periphery.

9. A device as claimed in claim 7, further comprising a ratchet mechanism to allow movement of the disk in only one direction.

10. A device as claimed in claim 1, wherein the closure pad is lifted away from the surface of said disk by engagement with a ramp.

11. A device as claimed in claim 1, further comprising a removable mouthpiece cover which, when in place, engages with the medicament holder to prevent movement thereof.

12. A device as claimed in claim 1, wherein the outlet comprises a conduit in which are arranged a plurality of staggered plates extending into the conduit from opposite sides of the conduit at an angle of less than 90° to the sides of the conduit and which plates are inclined towards the outlet to create a plurality of constrictions within the conduit and a plurality of changes in the direction of the airflow through the conduit.

13. A device as claimed in claim 12 comprising 4 plates.

14. A device as claimed in claim 12, wherein said plates are inclined at an angle less than 70° to the longitudinal axis of the conduit in the direction of airflow.

15. A device as claimed in claim 14, wherein said plates are inclined at an angle in the range of 15° to 50°.

16. A device as claimed in claim 15, wherein said plates are inclined at an angle of 30°.

17. A device as claimed in claim 12, wherein the plurality of staggered plates includes a penultimate plate, and wherein said penultimate plate is shaped so that at some point along the penultimate plate it divides into at least a first face and a second face, the first face extending into the conduit and the second face extending toward the outlet substantially parallel to the longitudinal axis of the conduit.

18. A device as claimed in claim 1, wherein said pockets are filled with medicament.

19. A powder inhalation device comprising a housing containing a medicament, a conduit with an outlet extending into the housing through which a user can inhale to create an airflow through the conduit, a dosing unit for delivering a dose of the medicament to the conduit and baffles arranged within the said conduit to aid disintegration of powder agglomerates entrained in said airflow, wherein the baffles comprise a plurality of staggered linear plates extending into the conduit from opposite sides of the conduit at an angle of less than 90° to the sides of the conduit and are inclined towards the outlet to create a plurality of constrictions within the conduit and a plurality of changes in the direction of the said airflow through the conduit.

20. A device as claimed in claim 19, comprising 4 plates.

21. A device as claimed in claim 19 wherein said plates are inclined at an angle less than 70° to the longitudinal axis of the conduit in the direction of airflow.

22. A device as claimed in claim 21, wherein said plates are inclined at an angle in the range of 15° to 50°.

23. A device as claimed in claim 22 wherein said plates are inclined at an angle of 30°.

24. A device as claimed in claim 19, wherein the plurality of staggered plates includes a penultimate plate, and wherein the penultimate plate is shaped so that at some point along the penultimate plate it divides into at least a first face and a second face, the first face extending into the conduit and the second face extending towards the outlet substantially parallel to the longitudinal axis of the conduit.

25. A device as claimed in claim 1 wherein the medicament is zanamivir.

26. An inhalation device of claim 1, wherein said holder defining said pocket and said pad are configured such that said holder and said pad are maintained in a fixed position relative to each other when said pocket is open.

27. The inhalation device of claim 1 wherein said closure pad and said holder form a seal where the contact, said seal being substantially impermeable to moisture.

28. A powder inhalation device comprising a housing containing:

a. a medicament;

b. a conduit with an outlet extending into the housing through which a user can inhale to create an airflow through the conduit;

c. a dosing unit for delivering a dose of the medicament to the conduit; and d. baffles arranged within the conduit;

wherein said baffles comprise a plurality of staggered plates extending into the conduit from opposite sides of the conduit to create a plurality of constrictions within the conduit and a plurality of changes in the direction of the airflow through the conduit, and wherein each of said staggered plates comprises a surface inclined towards the outlet at an angle of less than 90° to the sides of the conduit, said surface lacking any point along its length being at an angle of 90° or more to the sides of the conduit.

* * * * *